(12) United States Patent
Terry

(10) Patent No.: US 12,239,397 B2
(45) Date of Patent: Mar. 4, 2025

(54) ASSISTED DRIVE MODE WITH DAMPING FUNCTION FOR ROBOTIC IMAGING SYSTEM

(71) Applicant: Alcon Inc., Fribourg (CH)

(72) Inventor: Patrick Terry, Goleta, CA (US)

(73) Assignee: Alcon Inc., Fribourg (CH)

( * ) Notice: Subject to any disclaimer, the term of this patent is extended or adjusted under 35 U.S.C. 154(b) by 267 days.

(21) Appl. No.: 17/902,430

(22) Filed: Sep. 2, 2022

(65) Prior Publication Data

US 2023/0086411 A1    Mar. 23, 2023

Related U.S. Application Data

(60) Provisional application No. 63/243,939, filed on Sep. 14, 2021.

(51) Int. Cl.
*A61B 34/30* (2016.01)
*A61B 90/00* (2016.01)

(52) U.S. Cl.
CPC ............ *A61B 34/30* (2016.02); *A61B 90/361* (2016.02); *A61B 2034/305* (2016.02); *A61B 2090/066* (2016.02)

(58) Field of Classification Search
CPC ......... A61B 34/30; A61B 34/74; A61B 34/77; A61B 90/25; A61B 90/361; A61B 90/50; A61B 2034/305; A61B 2034/742; A61B 2090/031; A61B 2090/064; A61B 2090/065; A61B 2090/066; A61B 2090/5025; A61B 2090/508
See application file for complete search history.

(56) References Cited

U.S. PATENT DOCUMENTS

| | | | |
|---|---|---|---|
| 2014/0039681 A1* | 2/2014 | Bowling | A61B 34/30 700/261 |
| 2019/0327394 A1* | 10/2019 | Ramirez Luna | H04N 23/51 |
| 2020/0281676 A1* | 9/2020 | Rohs | A61B 34/10 |
| 2021/0315652 A1* | 10/2021 | Henrywood | A61B 34/74 |

* cited by examiner

*Primary Examiner* — Jason Holloway
*Assistant Examiner* — Blake A Wood

(57) ABSTRACT

A robotic imaging system includes a camera configured to one or more images of a target site. The camera may be a stereoscopic camera configured to record a left image and a right image for producing at least one stereoscopic image of the target site. A robotic arm is operatively connected to the camera, the robotic arm being adapted to selectively move the camera relative to the target site. A sensor is configured to detect forces and/or torque imparted by a user for moving the stereoscopic camera and transmit sensor data. A controller is configured to receive the sensor data, the controller having a processor and tangible, non-transitory memory on which instructions are recorded. The controller is adapted to selectively execute an assisted drive mode, which includes determining a movement sequence for the robotic arm based in part on the sensor data and a damping function.

16 Claims, 4 Drawing Sheets

ASSISTED DRIVE MODE WITH DAMPING FUNCTION FOR ROBOTIC IMAGING SYSTEM

INTRODUCTION

The present disclosure relates generally to a robotic imaging system. More specifically, the disclosure relates to an assisted drive mode in a robotic imaging system. Various imaging modalities are commonly employed to image different parts of the human body. Robotic systems have been developed to improve the efficiency of medical procedures employing these imaging modalities. The robotic systems may incorporate an assisted drive system to assist users in operating the system. Previous assisted drive systems mapped the input of the user directly to the velocity of the output device. However, this results in a number of drawbacks, such as suboptimal preservation of the user input direction and frequent operation of the system in saturated speed limits. Additionally, it is possible to overload the assisted drive system when large magnitude forces are applied.

SUMMARY

Disclosed herein is a robotic imaging system having a camera configured to one or more images of a target site. The camera may be a stereoscopic camera configured to record left and right images for producing at least one stereoscopic image of the target site. A robotic arm is operatively connected to the camera, the robotic arm being adapted to selectively move the camera relative to the target site. The robotic imaging system includes a sensor configured to detect forces and/or torque imparted by a user for moving the camera. The sensor is adapted to transmit sensor data. A controller is configured to receive the sensor data, the controller having a processor and tangible, non-transitory memory on which instructions are recorded. The controller is adapted to selectively execute an assisted drive mode, which includes determining a movement sequence for the robotic arm based in part on the sensor data and a damping function.

The damping function may be dynamic and represented by a relation ($\ddot{X} = \alpha^* W + \gamma^* O(|W|)^* \dot{X}$), where $\ddot{X}$ is a second derivative of a state vector, $\alpha$ is a first calibration constant, W is a wrench vector, $\gamma$ is a second calibration constant, $O(|W|)$ is a damping operator, and $\dot{X}$ is a first derivative of the state vector. The state vector is based on a set of linear position coordinates and/or a set of rotational position coordinates of a current position of the robotic arm. The wrench vector is based on the input force vector representing the forces imparted by the user and/or the input torque vector representing the torque imparted by the user. The first calibration constant is applied to the wrench vector, the first calibration constant having a first value for the input force vector and a second value for the input torque vector.

The damping operator may be based on one or more damping curves. The damping operator determines an output force-damping vector and/or an output torque-damping vector based on an input force vector and an input torque vector, respectively. The second calibration constant is applied to the damping operator, the second calibration constant having one value for the input force vector and another value for the input torque vector.

Applying the damping function may include obtaining a sum of one or more damping curves and inputting the sum into a hysteresis filter. The hysteresis filter is adapted to permit an output damping value to increase at a same rate as an input force vector representing the forces and/or an input torque vector representing the torque imparted by the user. The hysteresis filter is adapted to prevent the output damping value from decreasing at the same rate as the input force vector and/or the input torque vector.

The robotic arm may include one or more joints. The controller is configured to selectively command the one or more joints to rotate based on the movement sequence via respective motor control signals. The movement sequence specifies a rotation direction, a speed, and a duration of movement for the one or more joints of the robotic arm. The robotic arm may include one or more joints and a coupling interface connected to the one or more joints, the sensor being positioned at the coupling interface. The sensor may include a six-degrees-of-freedom haptic force-sensing device. The controller may be configured to determine at least one scale factor based on respective joint angles between the one or more joints of the robotic arm and/or joint limits. The controller may be configured to apply the scale factor to at least one joint speed of the movement sequence.

At least input device is operatively connected to the camera to allow a user to manually position the camera. The input device may include first and second control arms. The first and second control arms are operatively connected to the stereoscopic camera via a respective rotatable post, enabling the first and second control arms to be rotated with respect to the stereoscopic camera. The controller may be configured to provide force-application compensation for the sensor data to compensate for an offset between a respective location of the sensor and the at least one input device. The controller may be configured to provide gravity compensation for the sensor data.

Disclosed herein is a robotic imaging system having a stereoscopic camera configured to record a left image and a right image of a target site for producing at least one stereoscopic image of the target site. A robotic arm is operatively connected to the stereoscopic camera, the robotic arm being adapted to selectively move the stereoscopic camera relative to the target site. A sensor is configured to detect and transmit sensor data, including an input force vector representing forces imparted by a user and/or an input torque vector representing a torque imparted by the user for moving the stereoscopic camera. A controller is configured to receive the sensor data, the controller having a processor and tangible, non-transitory memory on which instructions are recorded. The controller is adapted to selectively execute an assisted drive mode, including determining a movement sequence for the robotic arm based in part on the sensor data and a damping function.

Applying the damping function includes permitting an output damping value to increase at a same rate as the input force vector and/or the input torque vector. Applying the damping function includes preventing the output damping value from decreasing at the same rate as the input force vector and/or the input torque vector. The damping function may be dynamic and represented by a relation ($\ddot{X} = \alpha^* W + \gamma^* O(|W|)^* \dot{X}$), where $\ddot{X}$ is a second derivative of a state vector, $\alpha$ is a first calibration constant, W is a vector based on the input force vector and/or the input torque vector, $\gamma$ is a second calibration constant, $O(|W|)$ is a damping operator, and $\dot{X}$ is a first derivative of the state vector.

The above features and advantages and other features and advantages of the present disclosure are readily apparent

Figure 1:
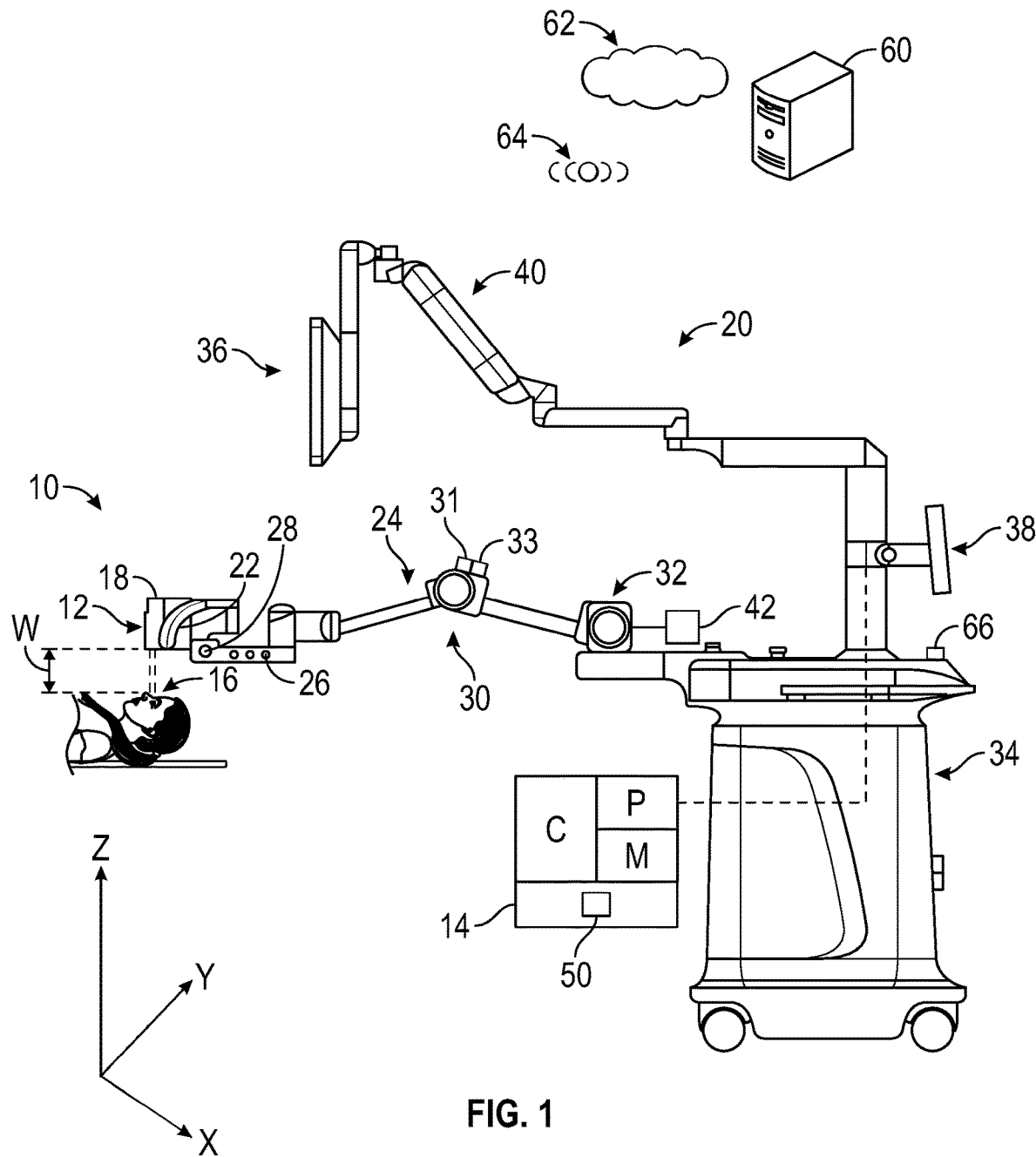
FIG. 1 is a schematic fragmentary diagram of a robotic imaging system having a camera, and a controller with an assisted drive mode.

Representative embodiments of this disclosure are shown by way of non-limiting example in the drawings and are described in additional detail below. It should be understood, however, that the novel aspects of this disclosure are not limited to the particular forms illustrated in the above-enumerated drawings. Rather, the disclosure is to cover modifications, equivalents, combinations, sub-combinations, permutations, groupings, and alternatives falling within the scope of this disclosure as encompassed, for instance, by the appended claims.

DETAILED DESCRIPTION

Referring to the drawings, wherein like reference numbers refer to like components, FIG. 1 schematically illustrates a robotic imaging system 10 having a camera 12 with an assisted drive mode 14. The robotic imaging system 10 is configured to image a target site 16. While the camera 12 shown in FIG. 1 is a stereoscopic camera 12, it is understood that other types of cameras may be employed (e.g., those taking a single image). Referring to FIG. 1, the stereoscopic camera 12 is at least partially located in a head unit 18 of a housing assembly 20, with the head unit 18 configured to be at least partially directed towards the target site 16. The stereoscopic camera 12 is configured to record first and second images of the target site 16, which may be employed to generate a live two-dimensional stereoscopic view of the target site 16. The target site 16 may be an anatomical location on a patient, a laboratory biological sample, calibration slides/templates, etc.

Figure 2:
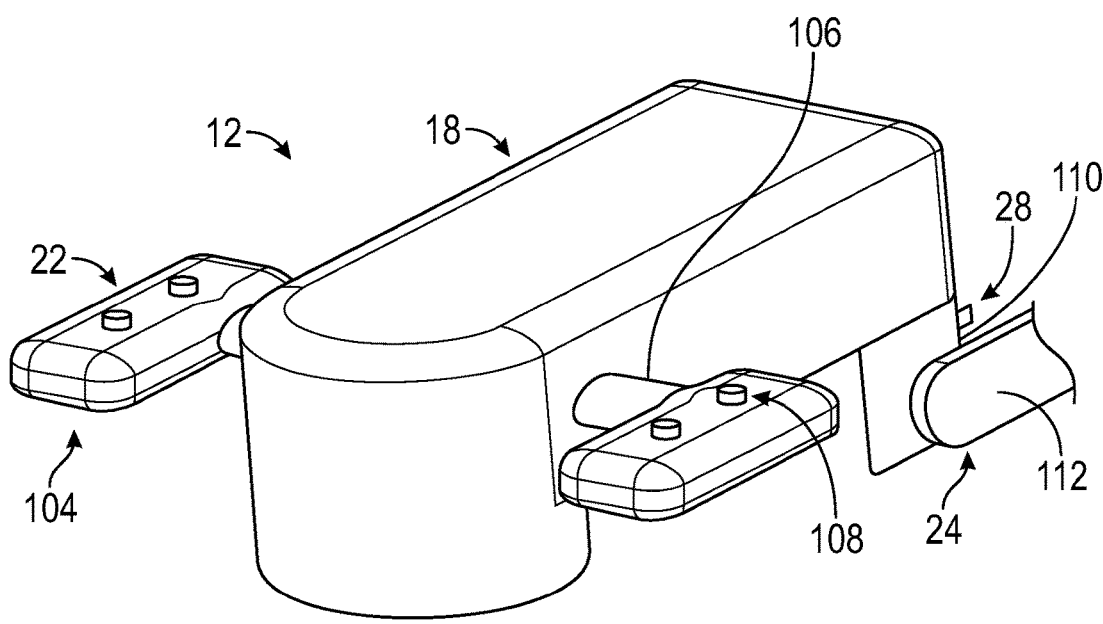
FIG. 2 is a schematic fragmentary perspective view of an input device employable in the robotic imaging system of FIG. 1.

Referring to FIG. 1, at least one input device 22 ("at least one" omitted henceforth) is operatively connected to the stereoscopic camera 12 (e.g., at the head unit 18) to allow a user to manually position the stereoscopic camera 12. An example implementation of an 'input device 22 is shown in FIG. 2. In the embodiment shown in FIG. 2, the input device 22 includes first and second control arms 102, 104. The first and second control arms 102, 104 may be connected to the head unit 18 via a respective rotatable post 106, enabling them to be rotated with respect to the head unit 18 (see FIG. 2). The first and second control arms 102, 104 may include respective controls 108 for activating or selecting specific features of the stereoscopic camera 12, such as focus, magnification, adjusting an amount/type of light projected onto the target site 16 and other features. It is understood that the number and form of the input devices 22 may be varied, for example, the input device 22 may include a joystick, wheel, mouse or touchscreen device. In some embodiments, the input device 22 may be controlled via a remote control 66 (see FIG. 1).

Referring to FIG. 1, the robotic imaging system 10 may include a robotic arm 24 operatively connected to and configured to selectively move the head unit 18. The head unit 18 may be mechanically coupled to the robotic arm 24 via a coupling plate 26. The user may position and orient the stereoscopic camera 12 with assistance from the robotic arm 24. Referring to FIG. 1, a sensor 28 may be operatively connected to the robotic arm 24 and/or coupling plate 26. The sensor 28 is configured to detect forces and/or torque imparted by a user for moving the stereoscopic camera 12, as shown in FIG. 2. The sensor 28 is configured to detect a user's movement or force on the stereoscopic camera 12 and convert the detected force/movement into rotational and/or translational data.

The robotic arm 24 may include one or more joints, such as first joint 30 and second joint 32, configured to provide further degrees of positioning and/or orientation of the head unit 18. The data from the sensor 28 may be employed to determine which joints of the robotic arm 24 are to be rotated and how quickly the joints should be rotated, in order to provide assisted movement of the stereoscopic camera 12 that corresponds to the forces/torques provided by the user. Referring to FIG. 1, a respective joint motor (such as joint motor 31) and a respective joint sensor (such as joint sensor 33), may be coupled to each joint. The joint motor 31 is configured to rotate the first joint 30 around an axis, while the joint sensor 33 is configured to transmit the position (in 3D space) of the first joint 30.

As described below, the assisted drive mode 14 incorporates a user-guided control system. In one embodiment, a user may hold the input device 22 and actuates or pushes a release button. Actuation of the release button causes the stereoscopic camera 12 to transmit a message to the controller C indicative that a user desires to begin the assisted drive mode 14. The controller C configures the robotic arm 24 and/or the coupling plate 26 to enable the user to gently steer the stereoscopic camera 12 in a desired direction. During this movement, the controller C causes the robotic arm 24 and/or the coupling plate 26 to move the stereoscopic camera 12 in a "power steering" manner, safely supporting its weight and automatically determining which joints should be activated and which should be braked in a coordinated manner to achieve the user's desired movement.

Referring to FIG. 1, the robotic imaging system 10 includes a controller C having at least one processor P and at least one memory M (or non-transitory, tangible computer readable storage medium) on which instructions are recorded for executing a method 200 (described below with respect to FIG. 4) of operating the assisted drive mode 14. The memory M can store controller-executable instruction sets, and the processor P can execute the controller-executable instruction sets stored in the memory M. The assisted drive mode 14 incorporates a damping function 50, via a particular set of dynamics, to infer user intent and stabilize unsteady user inputs.

In some embodiments, the robotic arm 24 may permit user movement without assistance, or at least initial assistance. In these other examples, the sensor 28 detects motion imparted by the user, which is used by the robotic imaging system 10 to subsequently cause one or more joints to rotate, thereby providing assisted movement. The time between initial detection of motion or the force resulting in the motion, until the robotic imaging system 10 causes the joints to rotate for a short time, e.g., less than 200 milliseconds, or as few as 10 milliseconds, where the user does not notice the initial time of unassisted movement of the robotic arm 24.

When users apply force to a force/torque driven 6 degree of freedom robotic system, the controller C may infer the user's intent from the sensor data. Many factors making this a very challenging problem, such as the sensor 28 not being collocated with user input and the sensor 28 suffering from nonlinear deformation effects due to being under load. Often without realizing it, users may apply far more force than needed to move the system. This is often due to "bear gripping" of the input device 22. Additionally, users may end up "fighting" the system when it does not move as they intend. When these problems arise during use, users typically begin to apply very large, detectable amounts of force and torque to the system, which can saturate the sensor input and make inferring the user intent very difficult. From a user's perspective, the robotic arm 24 is unstable.

The controller C is configured to analyze the magnitude of the user's input and use it to adjust dynamic damping terms that govern the dynamics used to set the trajectory of the assisted drive mode 14. The technical advantage provided is that the assisted drive mode 14 does not saturate easily and can be operated in both high and low acceleration regions.

The sensor 28 may include a six-degrees-of-freedom haptic force-sensing module. In these embodiments, the sensor 28 may detect translational force or motion in the X-axis, Y-axis, and Z-axis and separately detect rotational force or motion around a yaw-axis, a pitch-axis, and a roll-axis. The decoupling of the translational force and the rotational force may enable the robotic imaging system 10 to easily calculate direct and/or reverse kinematics for control of the robotic arm 24. The sensor 28 may include an opto-sensor (e.g., force/torque sensor) that enables the robotic arm 24 to respond electromechanically to a user's gentle push on the stereoscopic camera 12. The opto-sensor may include an electro-optical device configured to transform applied forces and/or torques into electrical signals, thereby enabling a desired force/torque input by a user to be sensed and transformed into a motion request that is provided in the sensed linear and/or rotational direction(s). It is understood that other types of sensor technologies may be employed. For example, the sensor 28 may include a strain gauge or piezoelectric device that is configured to sense a haptic signal from a user.

The position of the sensor 28 may be varied based on the application at hand. The sensor 28 may be located at an interface between the coupling plate 26 and the stereoscopic camera 12 for detecting the forces and/or torques imparted by a user via the input device 22. In the example shown in FIG. 2, the sensor 28 is positioned at a coupling interface 110 connected to a joint 112 of the robotic arm 24.

Referring to FIG. 1, the robotic arm 24 (and/or coupling plate 26) may be controlled via the controller C and/or an integrated processor, such as a robotic arm controller 42. The robotic arm 24 may be selectively operable to extend a viewing range of the stereoscopic camera 12 along an X-axis, a Y-axis and a Z-axis. The robotic arm controller 42 may include a processor, a server, a microcontroller, a workstation, etc. configured to convert one or more messages or instructions from the controller C into messages and/or signals that cause any one of the joints to rotate. The robotic arm controller 42 is also configured to receive and convert sensor information, such as joint position and/or speed from the robotic arm 24 and/or the coupling plate 26 into one or more messages for the controller C. U.S. application Ser. No. 16/398,014 (filed on Apr. 29, 2019), the contents of which is hereby incorporated by reference in its entirety, describes a stereoscopic visualization camera with an integrated robotics platform.

The head unit 18 may be connected to a cart 34 having at least one display medium (which may be a monitor, terminal or other form of two-dimensional visualization), such as first and second displays 36 and 38 shown in FIG. 1. Referring to FIG. 1, the controller C may be configured to process signals for broadcasting on the first and second displays 36 and 38. The housing assembly 20 may be self-contained and movable between various locations. The image stream from the stereoscopic camera 12 may be sent to the controller C and/or a camera processor (not shown), which may be configured to prepare the image stream for viewing. For example, the controller C may combine or interleave first and second video signals from the stereoscopic camera 12 to create a stereoscopic signal. The controller C may be configured to store video and/or stereoscopic video signals into a video file and stored to memory M. The first and second displays 36 and 38 may incorporate a stereoscopic display system, with a two-dimensional display having separate images for the left and right eye respectively. To view the stereoscopic display, a user may wear special glasses that work in conjunction with the first and second displays 36, 38 to show the left view to the user's left eye and the right view to the user's right eye.

Referring to FIG. 1, the first display 36 may be connected to the cart 34 via a flexible mechanical arm 40 with one or more joints to enable flexible positioning. The flexible mechanical arm 40 may be configured to be sufficiently long to extend over a patient during surgery to provide relatively close viewing for a surgeon. The first and second displays 36, 38 may include any type of display, such as a high-definition television, an ultra-high-definition television, smart-eyewear, projectors, one or more computer screens, laptop computers, tablet computers, and/or smartphones and may include a touchscreen.

The stereoscopic camera 12 is configured to acquire stereoscopic images of the target site 16, which may be presented in different forms, including but not limited to, captured still images, real-time images and/or digital video signals. "Real-time" as used herein generally refers to the updating of information at the same rate as data is received. More specifically, "real-time" means that the image data is acquired, processed, and transmitted at a high enough data rate and a low enough delay that when the data is displayed, objects move smoothly without user-noticeable judder or latency. Typically, this occurs when new images are acquired, processed, and transmitted at a rate of at least about 30 frames per second (fps) and displayed at about 60 fps and when the combined processing of the video signal has no more than about $1/30^{th}$ second of delay.

Figure 4:
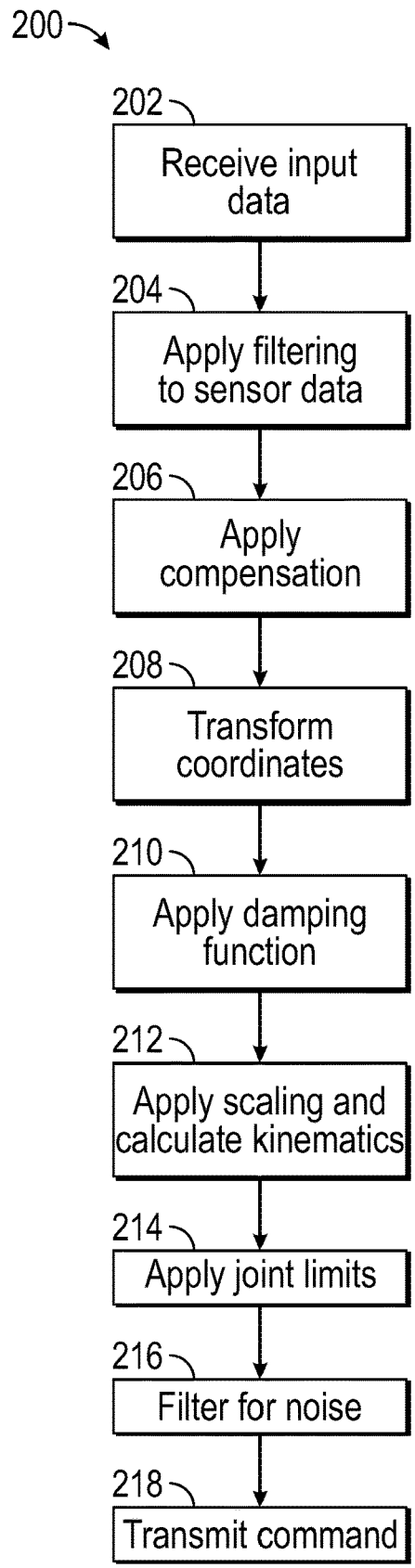
FIG. 4 is a flowchart of an example method for operating the assisted drive mode of FIG. 1.

Referring now to FIG. 4, a flowchart is shown of an example method 200 for operating the assisted drive mode 14 of FIG. 1. Method 200 may be embodied as computer-readable code or instructions stored on and partially executable by the controller C of FIG. 1. Method 200 need not be applied in the specific order recited herein and may be dynamically executed. Furthermore, it is to be understood that some steps may be eliminated. Method 200 may be executed periodically as force is applied to the stereoscopic camera 12 or at predefined time intervals.

Method 200 begins with block 202 of FIG. 4, where the controller C is programmed to receive input data, such as joint position data of the robotic arm 24 and sensor data from the sensor 28 related to force and/or torque imparted by a user on the stereoscopic camera 12. The sensor data includes a wrench vector (W), which is based on an input force vector representing the forces (Fx, Fy, Fz) imparted by the user and/or an input torque vector (τx, τy, τz) representing the torque imparted by the user, e.g., W=[Fx, Fy, Fz, τx, τy, τz].

Proceeding from block 202 to block 204 of FIG. 4, the controller C is programmed to apply filtering to the sensor data. The filtering may include applying a first low-pass filter, a second low pass filter, and/or a notch filter that targets cart vibrations. In other examples, a single low-pass filter and a notch filter may be used by the controller C. In some embodiments, no filtering is applied. This will reduce phase delay and increase responsiveness, however, a tradeoff would be additional noise in the joints.

Advancing from block 204 to block 206 in FIG. 4, the method 200 includes using the joint position data to provide compensation for the filtered sensor data (e.g., force/torque vector). The compensation may include gravity compensation and/or force-application point compensation. For gravity compensation, the effects of Earth's gravity are removed from the filtered sensor data. For force-application point compensation, the controller C provides compensation to the filtered sensor data (and/or gravity compensated sensor data) based on a point where the force was applied to the stereoscopic camera 12 (e.g., the input device 22). The sensor 28 may be located at an offset distance away and at an angle relative to the input device 22. The offset distance and angle cause the force applied at each of the input device 22 to be slightly shifted by direction and angle when detected in the sensor 28. The force-application compensation adjusts the force values as though the force was applied directly to the sensor 28 instead of the input device 22. The force-application compensation may be pre-determined based on a known angle and/or distance between the sensor 28 and the input device 22. Together, the gravity compensation and the force-application point compensation modify the filtered force/torque data to create a force/torque vector that is proportional to the force/torque provided by a user at the input device 22 of the camera.

Proceeding from block 206 to block 208 in FIG. 4, the method 200 includes transforming coordinates from the sensor (force/torque) frame to a global frame. The controller C is programmed to use the joint position data in conjunction with the compensated, filtered force/torque output data to perform a coordinate transform between the force/torque frame to a global frame or robot space. The transformation may include one or more predefined equations or relations based on the position and orientation of the sensor 28. The controller C is further adapted to use the joint position data to perform a coordinate transformation between a camera frame of the stereoscopic camera 12 and the global frame or robot space. The coordinate transformation for the camera frame may be based on optical calibration parameters mapped to robot space of the robotic arm 24.

Advancing from block 208 to block 210 in FIG. 4, the controller C is programmed to apply a damping function 50. In some embodiments, the damping function 50 is a non-linear dynamic function represented by a relation ($\ddot{X}=\alpha*W+\gamma*O(|W|)*\dot{X}$), where $\ddot{X}$ is a second derivative of a state vector, α is a first calibration constant, W is the wrench vector, γ is a second calibration constant, O(|W|) is a damping operator, and $\dot{X}$ is a first derivative of the state vector.

The state vector (X) is based on a set of linear position coordinates and/or a set of rotational position coordinates of a current position of the robotic arm 24, e.g., X=[x, y, z, Rx, Ry, Rz]. Each dot denotes a derivative, thus $\dot{X}$ represents velocity and $\ddot{X}$ represents acceleration. As noted above, the wrench vector (W) is based on an input force vector representing the forces (Fx, Fy, Fz) imparted by the user and/or an input torque vector (τx, τy, τz) representing the torque imparted by the user, e.g., W=[Fx, Fy, Fz, τx, τy, τz]. The state vector (X) is a kinematic location on the camera 12 that can be adjusted. In one example, the state vector (X) is set to coincide with the location on the input device 22 that the user is pressing. In another example, the state vector (X) is set to be a virtual point located inside the head unit 18 and centered between the first and second control arms 102, 104 (see FIG. 2).

The first calibration constant (α) is applied to the wrench vector. In some embodiments, the first calibration constant has a first value (α1) for the input force vector (Fx, Fy, Fz) and a second value (α2) for the input torque vector (τx, τy, τz). In a non-limiting example, the first value (α1) is between 0.05 and 0.65 and the second value (α2) is between 1.25 and 3.5. The second calibration constant (γ) is applied to the damping operator. In some embodiments, the second calibration constant has one value (γ1) for the three linear terms (from the forces) and another value (γ2) for the three rotational terms (from the torque). In a non-limiting example, one value (γ1) is between 1.0 and 3.4 and the other value (γ2) is between 1.25 and 2.75. The first calibration constant and second calibration constant represent user-settable resistance and sensitivity settings.

Figure 3:
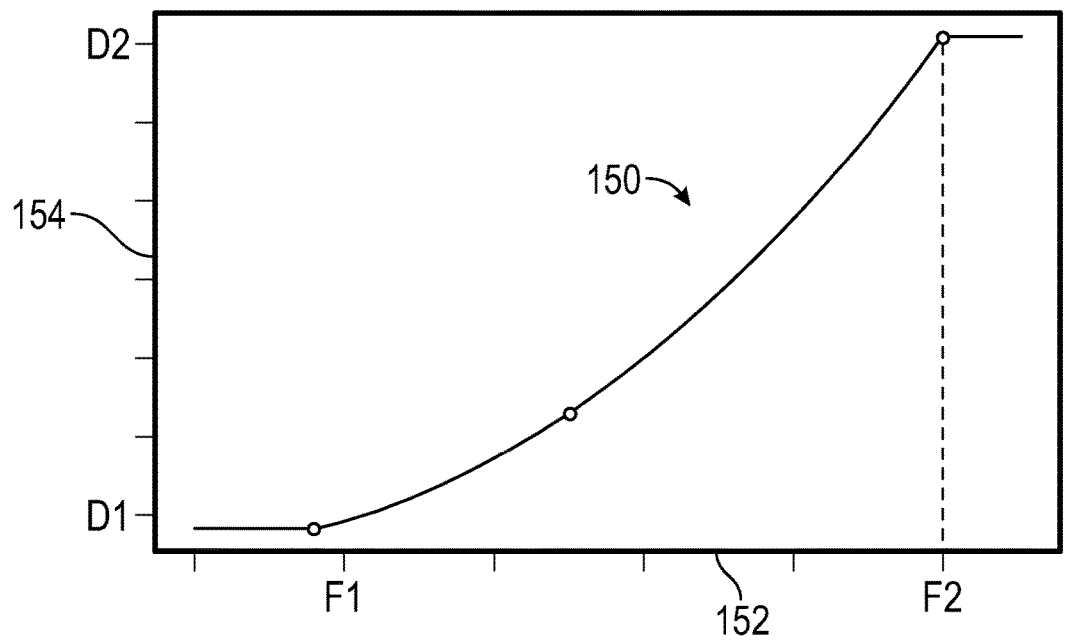
FIG. 3 is a schematic graph of an example damping curve, showing input force on the horizontal axis and output damping on the vertical axis.

The damping operator O(|W|) is based on one or more damping curves. FIG. 3 is a schematic example of one such damping curve 150, showing input force on the horizontal axis 152 and output damping on the vertical axis 154. Each of the damping curves has its own values for output damping, targeting a particular domain that maps to a damping coefficient for each component of the wrench vector W=[Fx, Fy, Fz, τx, τy, τz]. The damping operator O(|W|) determines an output force-damping vector and/or an output torque-damping vector based on an input force vector and an input torque vector, respectively. As shown in FIG. 3, as the input force increases from first force F1 to second force F2, the output damping increases from D1 to D2. Using the damping curve 150, as the user applies more force, the damping is increased in order to reduce the effect of the user's high acceleration on the control command. Several curves can be applied additively across different domains, to sum a total damping amount for each axis, that are potentially a function of different axes or external sensing. While the damping curve 150 shown in FIG. 3 trends upwards as force increases, it is understood that the trend or shape of the damping curve may be modified based on the application at hand.

Applying the damping function 50 includes obtaining a sum of the one or more damping curves and inputting the sum of the one or more damping curves into a hysteresis filter. The hysteresis filter permits the output damping value to increase at a same rate as the input force and/or the input torque but prevents the output damping value from decreasing at the same rate as the input force vector and/or input torque vector. This increases the damping time or decay time after the controller C detects large force inputs that caused the overall amount of damping in the system to increase.

Figure 5:
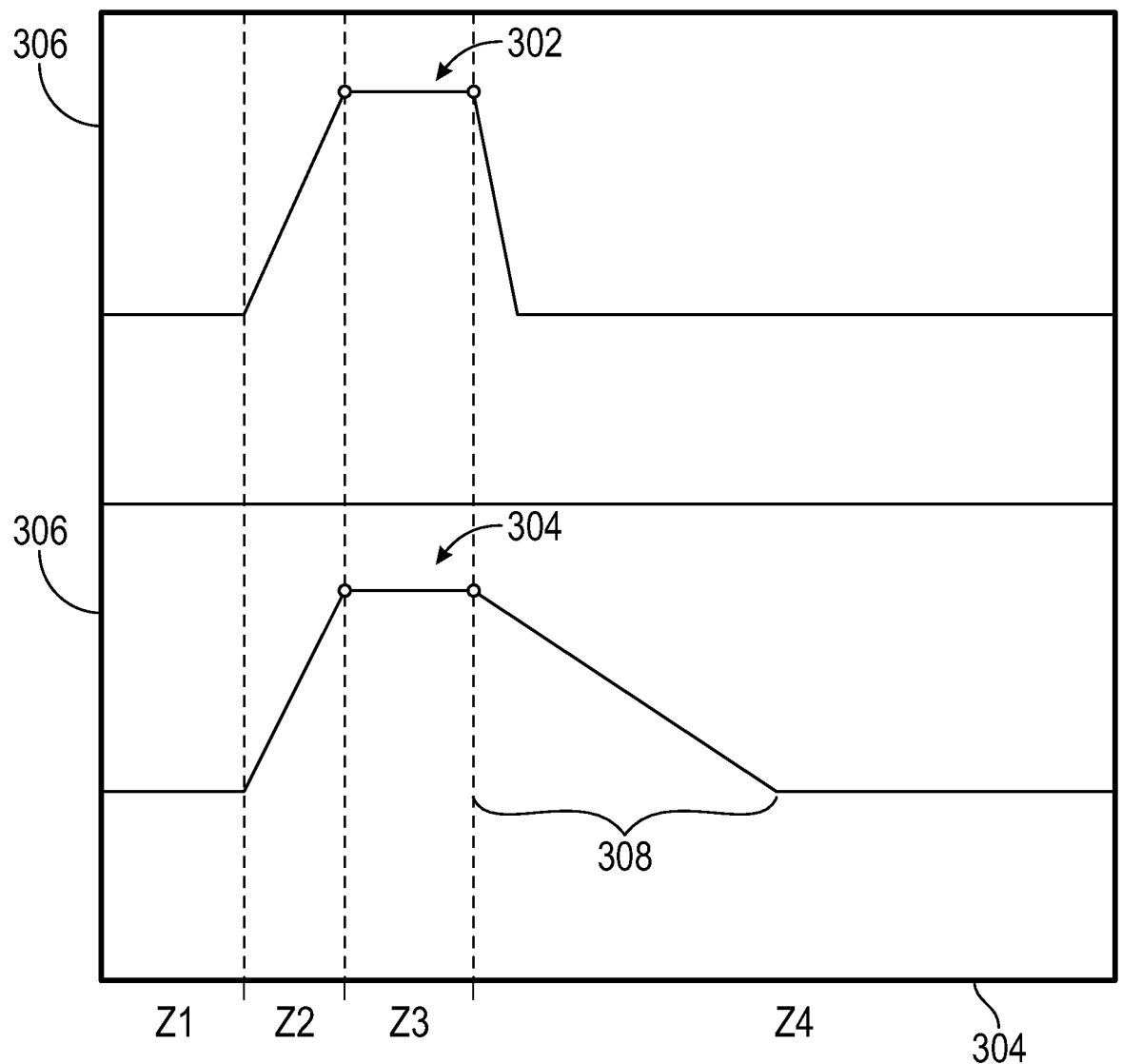
FIG. 5 is a schematic graph illustrating impact of a filter employable in the assisted drive mode of FIG. 1, with time on the horizontal axis and amplitude on the vertical axis.

FIG. 5 is a schematic graph illustrating impact of a hysteresis filter, with the upper trace representing input force 302 and the lower trace representing output damping 304. The horizontal axis 305 in FIG. 5 denotes time while the vertical axis 306 indicates amplitude. In time zones Z1 and Z3, both the input force 302 and the output damping 304 are flat. Referring to FIG. 5, as the input force 302 increases rapidly in time zone Z2, the output damping 304 is allowed to increase as well. In time zone Z4, as the input force 302 decreases rapidly, the output damping 304 is not allowed to decrease as rapidly as the input force 302, taking a longer time for the output damping 304 to decay. This results in the assisted drive mode 14 remaining damped for a longer damping time 308.

Proceeding from block 210 to block 212 of FIG. 4, method 200 may include various scaling applications (e.g., determining at least one scale factor). The scaling may include application of tool acceleration limits per component of d2X. For example, the maximum acceleration per axis has an allowable value. If one component is exceeded, that component is scaled down to the maximum value and all other components of acceleration are scaled by the same amount. The scaling may include application of sum acceleration limits, where the total acceleration is scaled down to keep the maximum sum of all components from exceeding a predefined limit. This feature may be employed in high acceleration inputs. The scaling may include application of tool velocity saturation limits. For example, if a component of the tool velocity dX (after the d2X integration step) exceeds a predefined limit, it is truncated to that limit.

Block 212 of FIG. 4 includes selecting a movement sequence using kinematics, for example, inverse kinematics and/or Jacobian kinematics (e.g., an inversion of a Jacobian matrix). The controller C determines a movement sequence that specifies how certain joints of the robotic arm and/or coupling plate 26 are to move in a coordinated manner and specifies, for example, joint rotation speed, joint rotational direction, and/or joint rotational duration. The movement sequence may also specify a sequence in which joints of the robotic arm 24 and/or the coupling plate 26 are to be rotated. Any of the joints of the robotic arm 24 and/or coupling plate 26 may rotate individually or have overlapping movement depending on the movement sequence. The Jacobian kinematic equations define how certain joints of the robotic arm 24 and/or the coupling plate 26 are to be moved based on the scaled translational/rotational vector(s). The Jacobian kinematics provide for velocity control while inverse kinematics provide for positional control. Other robotic arm control routines may be employed.

Proceeding from block 212 to block 214 of FIG. 4, method 200 may include applying joint limits, e.g., joint speed limits and joint position limits. After a movement sequence is determined, the controller C is configured to perform collision avoidance using joint speed scaling and/or boundaries. For example, the controller C may be configured to determine if the movement sequence will cause one or more joints and/or links of the robotic arm 24 and/or the coupling plate 26 to approach a boundary or other defined Cartesian limit, such as space around a patient or instrument. The controller C may compare estimates of positions of the links and/or joints in the robot space from the movement sequence to one or more defined boundaries and/or angle limits. Robot speeds are decelerated to zero as proximity to arbitrary joint limits are approached.

The controller C may validate a command to ensure that a command (or signal indicative of a command) is within operating parameters (e.g., duration, rotational speed, etc.) of a joint motor. The controller C and/or the robotic arm controller 42 may also validate a command by comparing the command to current thresholds to ensure the robotic arm 24 will not draw excess current during any phase of the movement sequence. For example, after the acceleration command ($\ddot{X}$) is calculated, acceleration limits are applied. Each axis (X, Y and Z) of the acceleration command has a maximum allowable value, and the total sum of the acceleration across the XYZ axes has a maximum allowable value. When a command is truncated due to being above the allowable commands, each axis is reduced by the same percentage as the truncated axis, to preserve the user's input direction vector.

Moving to block 216 of FIG. 4, the method 200 includes applying one or more anti-noise filters to the movement commands. The filter may include a high frequency low-pass filter that removes high frequency noise components, which may induce transient signals in a joint motor.

Per block 218 of FIG. 4, the controller C is programmed to transmit the commands via one or more signals to the appropriate joint motor of the robotic arm 24 and/or the coupling plate 26 according to the movement sequence. The transmitted commands cause motors at the respective joints to move the robotic arm 24 and/or the coupling plate 26, thereby causing the stereoscopic camera 12 to move as intended by the user. The method 200 may be repeated as long as a user applies force to the stereoscopic camera 12. Method 200 may be implemented directly at the joint torque level. For the case of a collaborative robot where such commands are not available, method 200 can be implemented by integrating a virtual acceleration command to produce a speed command which can be sent directly to the robotic arm controller 42.

The controller C of FIG. 1 may include or otherwise have access to information downloaded from remote sources and/or executable programs. Referring to FIG. 1, the controller C may be configured to communicate with a remote server 60 and/or a cloud unit 62, via a network 64. The remote server 60 may be a private or public source of information maintained by an organization, such as for example, a research institute, a company, a university and/or a hospital. The cloud unit 62 may include one or more servers hosted on the Internet to store, manage, and process data.

The network 64 may be a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data. The network 64 may be a Wireless Local Area Network (LAN) which links multiple devices using a wireless distribution method, a Wireless Metropolitan Area Network (MAN) which connects several wireless LANs or a Wireless Wide Area Network (WAN) which covers large areas such as neighboring towns and cities. Other types of connections may be employed.

The controller C of FIG. 1 may be an integral portion of, or a separate module operatively connected to the robotic imaging system 10. The controller C includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic media, a CD-ROM, DVD, other optical media, punch cards, paper tape, other physical media with patterns of holes, a RAM, a PROM, an EPROM, a FLASH-EEPROM, other memory chips or cartridges, or other media from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The flowcharts presented herein illustrate an architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by specific purpose hardware-based devices that perform the specified functions or acts, or combinations of specific purpose hardware and computer instructions. These computer program instructions may also be stored in a computer-readable medium that can direct a controller or other programmable data processing apparatus to function in a particular manner, such that the instructions stored in the computer-readable medium produce an article of manufacture including instructions to implement the function/act specified in the flowchart and/or block diagram blocks.

The numerical values of parameters (e.g., of quantities or conditions) in this specification, including the appended claims, are to be understood as being modified in each respective instance by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of each value and further divided ranges within the entire range. Each value within a range and the endpoints of a range are hereby disclosed as separate embodiments.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A robotic imaging system comprising:
a camera configured to record one or more images of a target site;
a robotic arm operatively connected to the camera, the robotic arm being adapted to selectively move the camera relative to the target site;
a sensor configured to detect and transmit sensor data representing forces imparted by a user and/or torque imparted by the user for moving the camera;
a controller configured to receive the sensor data, the controller having a processor and tangible, non-transitory memory on which instructions are recorded; and
wherein the controller is adapted to:
selectively execute an assisted drive mode, including determining a movement sequence for the robotic arm based in part on the sensor data and a damping function; and
apply the damping function including obtaining a sum of one or more damping curves and inputting the sum into a hysteresis filter;
the hysteresis filter is adapted to permit an output damping value to increase at a same rate as an input force vector representing the forces and/or an input torque vector representing the torque imparted by the user; and
the hysteresis filter is adapted to prevent the output damping value from decreasing at the same rate as the input force vector and/or the input torque vector.

2. The robotic imaging system of claim 1, wherein:
the camera is a stereoscopic camera configured to record a left image and a right image for producing at least one stereoscopic image of the target site.

3. The robotic imaging system of claim 1, wherein:
the damping function is dynamic and represented by a relation ($\ddot{X}=\alpha*W+\gamma*O(|W|)*\dot{X}$), where $\ddot{X}$ is a second derivative of a state vector, $\alpha$ is a first calibration constant, W is a wrench vector, $\gamma$ is a second calibration constant, $O(|W|)$ is a damping operator, and $\dot{X}$ is a first derivative of the state vector.

4. The robotic imaging system of claim 3, wherein:
the state vector is based on a set of linear position coordinates and/or a set of rotational position coordinates of a current position of the robotic arm.

5. The robotic imaging system of claim 3, wherein:
the wrench vector is based on the input force vector representing the forces imparted by the user and/or the input torque vector representing the torque imparted by the user.

6. The robotic imaging system of claim 5, wherein:
the first calibration constant is applied to the wrench vector, the first calibration constant having a first value for the input force vector and a second value for the input torque vector.

7. The robotic imaging system of claim 3, wherein:
the damping operator is based on one or more damping curves; and the damping operator determines an output force-damping vector and/or an output torque-damping vector based on an input force vector and an input torque vector, respectively.

8. The robotic imaging system of claim 7, wherein:
the second calibration constant is applied to the damping operator, the second calibration constant having one value for the input force vector and another value for the input torque vector.

9. The robotic imaging system of claim 1, wherein:
the robotic arm includes one or more joints;
the controller is configured to selectively command the one or more joints to rotate based on the movement sequence via respective motor control signals; and
the movement sequence specifies a rotation direction, a speed, and a duration of movement for the one or more joints of the robotic arm.

10. The robotic imaging system of claim 1, further comprising:
At least one input device operatively connected to the camera to allow a user to manually position the camera.

11. The robotic imaging system of claim 10, wherein:
the at least one input device includes first and second control arms; and
wherein the first and second control arms are operatively connected to the stereoscopic camera via a respective rotatable post, enabling the first and second control arms to be rotated with respect to the stereoscopic camera.

12. The robotic imaging system of claim 10, wherein:
the controller is configured to provide force-application compensation for the sensor data to compensate for an offset between a respective location of the sensor and the at least one input device.

13. The robotic imaging system of claim 1, wherein:
the controller is configured to provide gravity compensation for the sensor data.

14. The robotic imaging system of claim 1, wherein:
the robotic arm includes one or more joints and a coupling interface connected to the one or more joints, the sensor being positioned at the coupling interface.

15. The robotic imaging system of claim 1, wherein:
the sensor includes a six-degrees-of-freedom haptic force-sensing device.

16. The robotic imaging system of claim 1, wherein:
the robotic arm includes one or more joints, the controller being configured to determine at least one scale factor based on respective joint angles between the one or more joints of the robotic arm and/or joint limits; and
the controller is configured to apply the scale factor to at least one joint speed of the movement sequence.

* * * * *